United States Patent
Narisada et al.

(10) Patent No.: US 8,186,606 B2
(45) Date of Patent: May 29, 2012

(54) DEODORANT/FRAGRANT DEVICE, VOLATILIZING MATERIAL FOR USE IN THE SAME, PROCESS FOR PRODUCING THE VOLATILIZING MATERIAL, AND METHOD OF DEODORIZING/PERFUMING

(75) Inventors: Naoyuki Narisada, Shinjyuku-ku (JP); Ryuji Nomura, Shinjyuku-ku (JP)

(73) Assignee: S.T. Corporation, Tokyo (JP)

( * ) Notice: Subject to any disclaimer, the term of this patent is extended or adjusted under 35 U.S.C. 154(b) by 398 days.

(21) Appl. No.: 12/517,074

(22) PCT Filed: Nov. 29, 2007

(86) PCT No.: PCT/JP2007/073010
§ 371 (c)(1),
(2), (4) Date: Jun. 1, 2009

(87) PCT Pub. No.: WO2008/066094
PCT Pub. Date: Jun. 5, 2008

(65) Prior Publication Data
US 2010/0061886 A1   Mar. 11, 2010

(30) Foreign Application Priority Data
Nov. 30, 2006   (JP) ................. 2006-323699

(51) Int. Cl.
*A61L 9/04* (2006.01)
(52) U.S. Cl. ............. 239/44; 239/34; 422/5; 422/120
(58) Field of Classification Search .......... 422/5, 120; 239/34, 44
See application file for complete search history.

(56) References Cited

U.S. PATENT DOCUMENTS
4,739,928 A * 4/1988 O'Neil .................... 239/45

FOREIGN PATENT DOCUMENTS

| JP | 02102655 A | * | 4/1990 |
|---|---|---|---|
| JP | 5 156510 | | 6/1993 |
| JP | 3013371 | | 4/1995 |
| JP | 2005 329 | | 1/2005 |
| JP | 2005 40593 | | 2/2005 |
| JP | 2005 40594 | | 2/2005 |
| JP | 2005 40595 | | 2/2005 |
| JP | 2006249615 A | * | 9/2006 |
| JP | 2006 280907 | | 10/2006 |
| JP | 2007-105447 | * | 4/2007 |
| JP | 2007 105447 | | 4/2007 |

OTHER PUBLICATIONS

Derwent Abstract for JP 02102655 A, Apr. 1990.*
Derwent Abstract for JP 2006249615 A, inventor: Kunimoto, publsihed: Sep. 2006.*
English abstract for JP 2007-105447, invnetor: Nishi, published: Apr. 2007.*

* cited by examiner

*Primary Examiner* — Sean E Conley
(74) *Attorney, Agent, or Firm* — Oblon, Spivak, McClelland, Maier & Neustadt, L.L.P.

(57) ABSTRACT

The present invention is directed to a deodorant/fragrant device with reduced adsorption of the fragrance and other ingredients contained in a fragrant liquid, having both excellent deodorizing function and perfuming function, wherein a fragrant liquid contained in a container is absorbed by a wick and the fragrant liquid absorbed is volatilized and released from the container through a volatilizing material placed in contact with the wick, wherein a zinc compound is carried on the volatilizing material.

20 Claims, 2 Drawing Sheets

DEODORANT/FRAGRANT DEVICE, VOLATILIZING MATERIAL FOR USE IN THE SAME, PROCESS FOR PRODUCING THE VOLATILIZING MATERIAL, AND METHOD OF DEODORIZING/PERFUMING

CROSS-REFERENCE TO RELATED APPLICATIONS

This application is a 371 of PCT/JP07/073,010 filed Nov. 29, 2007 and claims the benefit of JP 2006-323699 filed Nov. 30, 2006.

TECHNICAL FIELD

The present invention relates to a deodorant/fragrant device, a volatilizing material for use in the same, a process for producing the volatilizing material, and a method of deodorizing/perfuming. More particularly, it relates to a deodorant/fragrant device that can exhibit excellent deodorizing effect without decreasing perfuming function of the deodorant/fragrant device, a volatilizing material for use in the same, a process for producing the volatilizing material, and a method of deodorizing/perfuming.

BACKGROUND ART

Conventionally, a deodorant/fragrant device is widely used to deodorize bad odor in living space such as rooms, bathrooms and entrances and impart a fragrance to the circumference. As the fragrant device of these, a device using a fragrance in various forms such as gel, liquid, solid and the like is proposed. However, at present, a fragrant device using a liquid fragrance is mainly used.

The fragrant device using the liquid fragrance generally has a mechanism as illustrated in FIG. 4. That is, a wick for absorbing a fragrant liquid is inserted in an opening of a container Aa such that one end thereof is dipped in the fragrant liquid contained in the container and the other end is exposed from the opening of the container Aa, and the fragrant liquid is volatilized and released into the air using a volatilizing member including a volatilizing material e provided in the end of the wick exposed from the opening.

The wick a is generally prepared by forming fibers such as pulp or synthetic fibers into a columnar shape, and absorbs the fragrant liquid through capillary action to lead the fragrant liquid to the volatilizing material e. The volatilizing material e is obtained by mixing fibers such as pulp with a heat fusible binder and the like, and forming the mixture into a plate-like shape by thermal compression, and volatilizes and releases the fragrant liquid carried through the wick a to impart a fragrance to a space.

It has been proposed to incorporate particles of an activated carbon into a volatilization member for the purpose of further imparting deodorizing effect to the fragrant device which volatilizes and releases an aromatic liquid (see Patent Document 1). However, in the fragrant device having an activated carbon contained in the volatilization member, the activated carbon adsorbs not only malodorous components, but components such as perfumes contained in a fragrant liquid. As a result, this rather gives rise to the problem that not only the perfuming function is decreased, but deodorizing function is not sufficiently exhibited.

To solve this problem, a technology of suppressing adsorption of a perfume on an activated carbon by incorporating a compound represented by a specific structural formula such as 3-methoxy-3-methyl-1-butanol into a fragrant liquid has been disclosed (see Patent Document 2). Furthermore, a fragrant liquid using a specific fragrance ingredient such as 2,4,6-trimethyl-2-phenyl-1,3-dioxane and a fragrant liquid using a surfactant having a specific structure has been proposed (see Patent Documents 3 and 4). However, in these technologies, the degree of freedom in formulation of a fragrant liquid is limited, and it is difficult to sufficiently increase preference of fragrance.

Patent Document 1: JP-A-2005-329
Patent Document 2: JP-A-2005-40593
Patent Document 3: JP-A-2005-40594
Patent Document 4: JP-A-2005-40595

DISCLOSURE OF THE INVENTION

Problems that the Invention is to Solve

Accordingly, development of a deodorant/fragrant device with reduced adsorption of the fragrance and other ingredients in a fragrant liquid and is excellent in both deodorizing function and perfuming function has been demanded.

Means for Solving the Problems

As a result of intensive investigations on a deodorant/fragrant device in which both effects of deodorizing function and perfuming function are sufficiently exhibited, the present inventors have found that the above problems can be solved by using a volatilizing material carrying a specific deodorant, and have reached to complete the present invention.

That is, the present invention provides a deodorant/fragrant device, wherein a fragrant liquid contained in a container is absorbed by a wick and the fragrant liquid absorbed is volatilized and released from the container through a volatilizing material placed in contact with the wick, and wherein a zinc compound is carried on the volatilizing material.

The present invention further provides a volatilizing material for a fragrant liquid, comprising a fiber molded article carrying a zinc compound, and a process for producing the same.

The present invention further provides a method of deodorizing/perfuming, wherein that a zinc compound is present in a portion where a fragrant liquid is volatilized.

Advantage of the Invention

In the deodorant/fragrant device of the present invention, the fragrance and other ingredients adsorption on a volatilizing material is reduced and thus the decrease in perfuming effect and deodorizing effect can be suppressed, as compared with a device in which an activated carbon is contained in a volatilizing material. As a result, removal of bad odor and imparting fragrance can simultaneously be conducted, and its effect is sustained over a long period of time.

Furthermore, in the deodorant/fragrant device of the present invention, because the fragrance and other ingredients adsorption on a volatilizing material is reduced as described above, the formulation of a fragrant liquid is not limited, and flexible product designing is possible.

BEST MODE FOR CARRYING OUT THE INVENTION

The deodorant/fragrant device of the present invention is characterized in that a volatilizing material carrying a zinc compound is used in a general fragrant device using a fragrant liquid, that is, in a deodorant/fragrant device wherein a fragrant liquid contained in a container is absorbed by a wick and the fragrant liquid absorbed is volatilized and released from the container through a volatilizing material placed in contact with the wick.

In the present invention, any zinc compound conventionally used as a deodorant can be used and carried on the volatilizing material. A zinc compound which is insoluble or sparingly soluble in water is preferable because it does not dissolve in the fragrant liquid and thus not desorb from the volatilizing material.

On the other hand, a solid zinc compound is preferable due to ease of carrying on the volatizing material. Specifically, the zinc compound includes zinc oxide, zinc aluminum oxide, zinc silicate, zinc aluminum silicate, layered zinc aluminosilicate, zinc 2-ethylhexanoate and zinc ricinolate. Among them, zinc oxide, zinc aluminum oxide, zinc silicate, zinc aluminum silicate and layered zinc aluminosilicate, which are solid and insoluble or sparingly soluble in water are preferably used.

Among the above zinc compounds, the zinc aluminum oxide is a compound represented by $ZnO.Al_2O_3$, and the commercially available products such as SEABIO Z-24 (manufactured by Seawater Chemical Institute, Inc.) can be used. The zinc aluminum silicate is a compound represented by $ZnO.Al_2O_3.SiO_2$, and the commercially available products such as SEADEO KZ-4 (manufactured by Seawater Chemical Institute, Inc.) can be used.

The layered zinc aluminosilicate is a compound having a layered structure represented by the formula $(Zn_{6-n}Al_n)(Si_{4-n}Al_n)O_{10}(OH)_8.nH_2O$, and this compound may be used alone in the present invention. Also, a product in which layered zinc aluminosilicate is carried on inorganic particles such as amorphous silica particles in the form of a single layer or a multilayer (for example, represented by $5ZnO.Al_2O_3.3SiO_2.5H_2O/4SiO_2$) can be used. The commercially available products of the layered zinc aluminosilicate such as MIZUKANITE (manufactured by Mizusawa Industrial Chemicals, Ltd.) and LIGNITE (manufactured by Lion Corporation) can be used.

As the volatilizing material, the conventional volatilizing materials can be used. For example, two non-woven fabrics are used, a fiber layer obtained by mixing fibers and a heat-fusible binder by the conventional web formation method such as air-laid method is formed on one non-woven fabric (a substrate), the fiber layer is covered with another non-woven fabric (a covering body), the resulting assembly is dried by, for example, a method of passing through a through air drier, followed by bonding and molding by a hot calender system or a hot embossing system. The zinc compound may be carried on the volatilizing material by the conventional carrying method, preferably by any one of the following methods.

A process for producing a volatilizing material of a type shown in FIG. 1 includes a process in which a zinc compound is mixed with fibers and a heat-fusible binder, the resulting mixture is laminated on a non-woven fabric (a substrate, lower surface of FIG. 1) by the conventional web formation method such as air-laid method to form a fiber layer, the fiber layer is covered with a non-woven fabric (a covering body), and a volatilizing material is molded according to the conventional method (production process 1).

A process for producing a volatilizing material of a type shown in FIG. 2 includes a process in which fibers and a heat-fusible binder are mixed, the resulting mixture is laminated on a non-woven fabric (a substrate) by the conventional web formation method such as air-laid method to form a fiber layer, a zinc compound is sprayed, together with a binder if necessary, on the fiber layer, the fiber layer is covered with a non-woven fabric (a covering body), and a volatilizing material is molded according to the conventional method (production process 2).

A process for producing a volatilizing material of another type includes a process in which a zinc compound is sprayed, together with a binder if necessary, on a non-woven fabric (a substrate), a mixture of fibers and a heat-fusible binder are laminated thereon by the conventional web formation method to form a web, the web is covered with a non-woven fabric (a covering body), and a volatilizing material is molded according to the conventional method (production process 3). In this case, the volatilizing material is used such that the substrate side becomes an upper surface. An air-permeable material such as woven fabrics, non-woven fabrics and papers can be used as the substrate and the covering body.

In the above each process, the fibers used in the fiber layer include the conventional fibers, for example, long fibers or short fibers of polyethylene, polypropylene, pulp, rayon, cellulose, acetate, acryl, nylon, vinylon, polyester, polyvinyl chloride, wool, cotton, silk and the like, which may be used alone or as mixtures of two or more.

In addition to the fibers, a binder such as polyethylene, polypropylene, polyvinyl alcohol, polyester, acrylic resin, polyacrylonitrile, polyvinyl acetate, epoxy resin and polyurethane can be used for the fiber layer as necessary. A heat-fusible binder is preferably used. The form of the binder used includes a granular form and a fibrous form. The fibrous binder that can be used includes multi-component type heat-fusible fibers such as polyethylene/low melting polyethylene core-shell composite fibers, polypropylene/polyethylene core-shell composite fibers, polyester/polyethylene core-shell composite fibers, polyester/low melting polyester core-shell composite fibers, polypropylene/polyvinyl alcohol core-shell composite fibers, and polyethylene/polyvinyl alcohol core-shell composite fibers.

The non-woven fabric used as a substrate or a covering body includes non-woven fabrics formed of polyethylene, polypropylene, pulp, rayon, cellulose, acetate, acryl, nylon, vinylon, polyester, polyvinyl chloride, wool, cotton, silk and the like.

Among the above production processes, the production process 1 (FIG. 1) enables the zinc compound to be carried in larger amount. However, the zinc compound B is carried in the fiber layer A, and the zinc compound entered in the inside of the volatilizing material tends to contribute less to deodorizing effect. By contrast, in the production processes 2 (FIG. 2) and 3, the zinc compound B is carried between the non-woven fabric C (a covering body or a substrate) and the fiber layer A, and this is preferred from the standpoint of deodorizing efficiency. Particularly, in the production process 3, the zinc compound can be carried more proximally to the surface of the volatilizing material, and this is further preferred.

The amount of the zinc compound carried on the volatilizing material of the present invention can appropriately be selected. The amount is 0.1 g/m² to 1,000 g/m², preferably 1 g/m² to 100 g/m², and more preferably 1 g/m² to 10 g/m². When the amount is larger than 1,000 g/m², volatilization of fragrance ingredients is suppressed, and sufficient perfuming effect is not obtained. When the amount is less than 0.1 g/m², sufficient deodorizing effect is not obtained.

The average particle diameter of the zinc compound is 0.1 µm to 10 mm, preferably 1 µm to 1 mm, and more preferably 1 µm to 100 µm. When the average particle diameter is larger than 10 mm, it is difficult for the volatilizing material to carry the zinc compound, and dropout may be generated. When the average particle diameter is smaller than 0.1 µm, an inorganic deodorant containing zinc enters in the inside of the volatilizing material even in the case where the volatilizing material is produced by the production process 2 or 3, and it is difficult for the volatilizing material to carry the zinc compound on the surface thereof.

The volatilizing material which is separated from the wick for absorbing a fragrant liquid is described above, but it is apparent that even though the volatilizing material and the wick are united, the effect of the present invention can be obtained so long as the zinc compound is carried on the volatilizing material. In this case, the zinc compound may not be carried on the wick portion, but it is necessary that the zinc compound is carried at least on a part or the whole of the volatilizing material portion.

The volatilizing material thus obtained is used in a general fragrant device using a fragrant liquid without any specific limitation as described above. That is, any of a wide variety of the conventional products can be used as the container for the fragrant liquid, the wick inserted in the container, and the like of the present invention without limitation regarding the form and structure.

As the fragrant liquid used in the present invention, the conventional fragrant liquids can also be used, and the major composition example includes a fragrant liquid obtained by solubilizing and emulsifying fragrance ingredients in water using a surfactant.

As the fragrance ingredient, any of natural perfume and artificial perfume can be used, and it may be a blended perfume. Furthermore, any of animal perfume and vegetable perfume can be used. Examples of the animal perfume include musk, civet and ambergris. Examples of the vegetable perfume include abies oil, ajowan oil, almond oil, angelica root oil, basil oil, bergamot oil, birch oil, rosewood oil, cajuput oil, cananga oil, capsicum oil, caraway oil, cardamom oil, cassia oil, celery oil, cinnamon oil, citronella oil, cognac oil, coriander oil, cumin oil, camphor oil, dill oil, estragon oil, eucalyptus oil, fennel oil, garlic oil, ginger oil, grapefruit oil, hop oil, lemon oil, lemongrass oil, nutmeg oil, mandarin oil, mentha oil, orange oil, sage oil, star anis oil and turpentine oil.

The artificial perfume is a synthetic perfume or an extracted perfume, and examples thereof include hydrocarbon type perfume such as pinene and limonene; alcohol type perfume such as linalool, geraniol, citronellol, menthol, borneol, benzyl alcohol, anisyl alcohol and β-phenethyl alcohol; phenol type perfume such as anethole and eugenol; aldehyde type perfume such as n-butyl aldehyde, isobutylaldehyde, hexyl aldehyde, citral, citronellal, benzaldehyde and cinnamic aldehyde; ketone type perfume such as carvone, menthone, camphor, acetophenone and ionone; lactone type perfume such as γ-butyrolatone, coumarin and cineole; and ester type perfume such as octyl acetate, benzyl acetate, cinnamyl acetate, butyl propionate and methyl benzoate. A blended perfume comprising a mixture of two or more of the above perfumes can be used.

The amount of the perfume is 0.01 to 30% by mass, preferably 0.1 to 20% by mass, and more preferably 1 to 15% by mass, based on the mass of the composition.

As the surfactant, the conventional anionic surfactant, cationic surfactant, nonionic surfactant and ampholytic surfactant can be used alone or as mixtures of two or more.

The anionic surfactant includes soap (higher fatty acid soap), basis material for soap, metallic soap, sodium alkyl benzene sulfonate, triethanolamine N-acyl-L-glutamate, sodium N-acyl-L-glutamate, sodium alkyl sulfate, polyoxyethylene alkyl ether sodium sulfate, polyoxyethylene alkyl phenyl ether sodium sulfate, sodium dialkyl sulfosuccinate, polyoxyethylene alkyl ether phosphoric acid, polyoxyethylene alkyl phenyl ether phosphoric acid, coconut oil fatty acid sodium methyltaurine (sodium N-cocoyl-N-methyltaurine), triethanolamine lauryl sulfate, sodium lauryl sulfate, sodium lauroyl sarcosine, sodium lauroyl methyl β-alanine liquid and sodium lauroyl methyltaurine, which may be used alone or as mixtures of two or more.

The cationic surfactant includes lanolin fatty acid aminopropylethyl dimethylammonium ethyl sulfate, alkyl trimethylammonium chloride, dialkyl dimethylammonium chloride, distearyl dimethylammonium chloride, stearyl dimethylbenzyl ammonium chloride, stearyl trimethylammonium chloride, benzalkonium chloride and benzethonium chloride, which may be used alone or as mixtures of two or more.

The nonionic surfactant includes polyoxyethylene alkyl ether, polyoxyethylene alkyl phenyl ether, polyoxyethylene styryl phenyl ether, polyoxyethylene alkyl aminoether, polyethylene glycol fatty acid ester, polyoxyethylene polyoxypropylene glycol, sorbitan fatty acid ester, polyoxyethylene sorbitan fatty acid ester, polyoxyethylene hardened castor oil ether, fatty acid alkanolamide and tertiary amine oxide, which may be used alone or as mixtures of two or more.

The polyoxyethylene alkyl ether has 3 to 18, and preferably 7 to 12 of polyoxyethylene chains. The alkyl chain may be a linear chain or a branched chain, and the alkyl chain length is 8 to 22, and preferably 12 to 14.

The polyoxyethylene alkyl phenyl ether has 3 to 18, and preferably 5 to 12 of polyoxyethylene chains. The alkyl chain may be a linear chain or a branched chain, and the alkyl chain length is 8 to 22, and preferably 12 to 14.

The fatty acid alkanolamide includes monoethanolamide and diethanolaminde of coconut oil fatty acid, stearic acid and lauric acid. The tertiary amine oxide includes lauryl dimethylamine oxide and coconut oil fatty acid dimethylamine oxide.

The ampholytic surfactant includes 2-alkyl-N-carboxymethyl-N-hydroxyethyl imidazolinium betaine, alkyl diaminoethyl glycine hydrochloride liquid and lauryl diemthylaminoacetic acid betaine, which may be used alone or as mixtures of two or more.

Among these surfactants, the anionic surfactant and/or nonionic surfactant are preferred due to their solubilization power and emulsification power.

The amount of the surfactant can appropriately be selected according to the kind and amount of the fragrance ingredients compounded. The amount is 0.01 to 30% by mass, preferably 0.1 to 20% by mass, and more preferably 0.5 to 15% by mass, based on the mass of the composition. When the amount is less than 0.01% by mass, the fragrance ingredient cannot be emulsified or solubilized, thereby affecting stability of the liquid fragrance.

The fragrant liquid used in the present invention can further contain a deodorant, thereby obtaining stronger deodorizing effect. The deodorant includes plant extracts, chlorine compounds, aldehyde compounds, organic acid compounds, cyclodextrin and surfactants.

The fragrant liquid of the present invention can further contain solvents such alcohol and glycol, solubilization aids, deodorants, gelling agents, thickeners, antifungal agents, antibacterial agents, ultraviolet absorbers, antioxidants, pigments and the like, if necessary, in a range that the effect of the present invention is not influenced.

EXAMPLES

The present invention will be described in more detail below by Production Examples and Examples, but the invention is not limited to these Production Examples and Examples.

Production Example 1

Production Process (1) of Volatilizing Material

A mixture of pulp (average fiber length: 1.5 mm), a powdery polyethylene as a binder, and a layered zinc aluminosilicate compound (MIZUKANITE HQ-048; particle diameter: 0.3-0.8 mm, manufactured by Mizusawa Industrial Chemicals, Ltd.) in an amount of 100 g per 1 m² was sprayed onto a pulp-made non-woven fabric, and another pulp-made non-woven fabric was placed thereon. The assembly was heated in an oven and passed through a hot embossing system to obtain a volatilizing material having a thickness of 10 mm of the present invention (invention product 1).

Production Example 2

Production Process (2) of Volatilizing Material

A mixture of pulp (average fiber length: 1.5 mm) and a powdery polyethylene as a binder was sprayed onto a pulp-made non-woven fabric, and a layered zinc aluminosilicate compound (MIZUKANITE HP; particle diameter: 3-5 μm, manufactured by Mizusawa Industrial Chemicals, Ltd.) was sprayed thereon in an amount of 15 g per 1 m². Another pulp-made non-woven fabric was then placed thereon. The assembly was heated in an oven and passed through a hot embossing system to obtain a volatilizing material having a thickness of 10 mm of the present invention (invention product 2).

Production Example 3

Production Process (3) of Volatilizing Material

A mixture of pulp (average fiber length: 1.5 mm) and a powdery polyethylene as a binder was sprayed onto a pulp-made non-woven fabric, and a layered zinc aluminosilicate compound (MIZUKANITE HQ-048; particle diameter: 0.3-0.8 mm, manufactured by Mizusawa Industrial Chemicals, Ltd.) was sprayed thereon in an amount of 20 g per 1 m². Another pulp-made non-woven fabric was then placed thereon. The assembly was heated in an oven and passed through a hot embossing system to obtain a volatilizing material having a thickness of 10 mm of the present invention (invention product 3).

Production Example 4

Production Process (4) of Volatilizing Material

A volatilizing material of the present invention (invention product 4) was obtained in the same manner as in Production Example 2, except that zinc oxide (particle diameter: 0.2-0.6 μm) was used in place of the layered zinc aluminosilicate.

Production Example 5

Production Process (5) of Volatilizing Material

A volatilizing material of the present invention (invention product 5) was obtained in the same manner as in Production Example 2, except that zinc aluminum oxide (trade name: SEABIO Z-24, average particle diameter: 5 μm, manufactured by Seawater Chemical Institute, Inc.) was used in place of the layered zinc aluminosilicate.

Production Example 6

Production Process (6) of Volatilizing Material

A volatilizing material of the present invention (invention product 6) was obtained in the same manner as in Production Example 2, except that zinc aluminum silicate (SEADEO KZ-4, average particle diameter: 1-5 μm, manufactured by Seawater Chemical Institute, Inc.) was used in place of the layered zinc aluminosilicate.

Example 1

Deodorant Test

A deodorant test was conducted using each of the volatilizing materials of the invention products 2, and 4 to 6. The volatilizing material obtained in each Production Example was cut into a size of 55 mm×55 mm and a thickness of 10 mm (about 5.0 g). The cut piece was impregnated with 25 g of a fragrant liquid prepared by the formulation shown in Table 1. The piece was placed in a 10 liter Tedler bag, and hydrogen sulfide gas as bad odor was injected into the bag. Bad odor concentration was measured 1 minute and 180 minutes after injection, and the odor eliminating rate was calculated by the following formula. A volatilizing material on which an inorganic deodorant containing zinc is not carried (comparison product 1), a volatilizing material on which coconut shell activated carbon (average particle diameter: 50 μm, iodine adsorbed amount: 1,500 mg/g, methylene blue adsorbed amount: 300 ml/g) is carried in place of the inorganic deodorant containing zinc (comparison product 2), and a volatilizing material on which artificial zeolite is carried in place of the inorganic deodorant containing zinc (comparison product 3) were used as comparison products. These products were obtained in the same manner as in Production Example 2. The results are shown in Table 2.

Odor eliminating rate (%)=$(A-B)/A \times 100$ wherein A is bad odor concentration (ppm) after 1 minute, and B is bad odor concentration (ppm) after 180 minutes.

TABLE 1

| | Ingredient | Amount (% by mass) |
|---|---|---|
| Perfume | Floral perfume blend (manufactured by Takasago International Corporation) | 1 |
| Surfactant | Polyoxyethylene (n = 7-14) alkyl ($C_8$-$C_{14}$) ether | 3 |
| Solvent | Ethanol | 3 |
| Water | Ion-exchanged water | Remainder |

TABLE 2

| | Invention product | | | | Comparison product | | |
|---|---|---|---|---|---|---|---|
| | 2 | 4 | 5 | 6 | 1 | 2 | 3 |
| Odor eliminating rate (%) | 60 | 82 | 62 | 56 | 8 | 30 | 28 |

As is apparent from the results, the invention products all exhibited excellent deodorant effect on hydrogen sulfide without influence from the fragrant liquid

Example 2

Functional Evaluation Test

The volatilizing material obtained in each of Production Examples 2, and 4 to 6 was cut into a size of 55 mm×55 mm and a thickness of 10 mm (about 5.0 g), and 400 g of the fragrant liquid shown in Table 1 was volatilized using a deodorant/fragrant device* of FIG. 3 (fragrant liquid impregnated amount in volatilizing material: about 25.0 g). At the initial stage of volatilization (1 day later) and the terminal stage of volatilization (60 days later), the fragrant liquid was volatilized in a space of 2 m³. Intensity of fragrance was evaluated with 10 panelists by the following standard, and its average value was obtained. The same test and evaluation were conducted for the comparison products 1 to 3. In the test, the comparison product 1 is a product on which a deodorant adsorbing fragrance ingredients is not carried. Therefore, this product was used as a control. The results are shown in Table 3.

* FIG. 3 is a partially cut sectional view of the deodorant/fragrant device used in Example 2. The device comprises a container 1, an inner plug 2, a wick 3 attached to the inner plug 2, a volatilizing material 32, and a diffusion cover material 30 having fragrance volatilizing holes 48, 49 and 57. An upper end 3a of the wick 3 is projected from the upper surface of the inner plug 2, and extended from an opening 6 of the container 1. On a holding member 31 provided in the opening 6, the volatilizing material 32 is provided so as to contact with the upper end 3a of the wick 3. A fragrant liquid is contained in the container 1. A lower end 3b of the wick 3 is dipped in the fragrant liquid, and soaks up the fragrant liquid. The fragrant liquid absorbed is brought to the volatilizing material 32, and the fragrance is vaporized from the volatilizing material 32, and volatilized and released in air from the fragrance volatilizing holes 48, 49 and 57 provided in the diffusion cover material 30.

(Evaluation Standard)
- 0: Scentless
- 1: Barely detectable scent
- 2: Weak scent but identifiable for its source
- 3: Readily detectable scent
- 4: Strong scent
- 5: Intense scent

TABLE 3

| | Invention product | | | | Comparison product | | |
|---|---|---|---|---|---|---|---|
| | 2 | 4 | 5 | 6 | 1 | 2 | 3 |
| Initial stage | 3.7 | 3.7 | 3.7 | 3.7 | 3.7 | 3.4 | 3.5 |
| Terminal stage | 2.7 | 2.7 | 2.7 | 2.7 | 2.7 | 1.7 | 1.9 |

From the above results, in the comparison products 2 and 3, intensity of fragrance was greatly decreased by the effect of adsorption to the deodorant at the terminal stage of volatilization. On the other hand, the invention products did not have substantial difference from the comparison product 1 even at the terminal stage of volatilization, and decease in intensity of fragrance by the effect of the deodorant was not observed.

INDUSTRIAL APPLICABILITY

The deodorant/fragrant device of the present invention has both excellent deodorizing function and perfuming function, and the effect is sustained over a long period of time. Therefore, the device can extremely advantageously be utilized.

Figure 1:
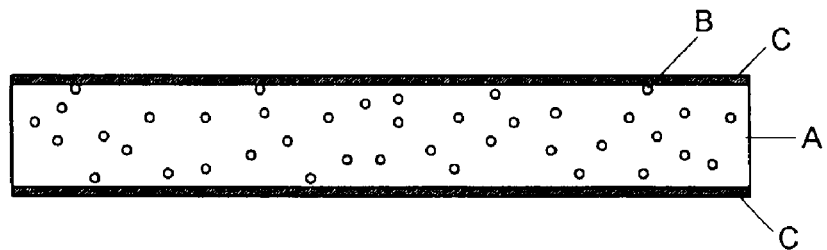
FIG. 1 is a sectional view of the volatilizing material of the present invention in which an inorganic deodorant containing zinc is carried in a fiber layer.
Figure 2:
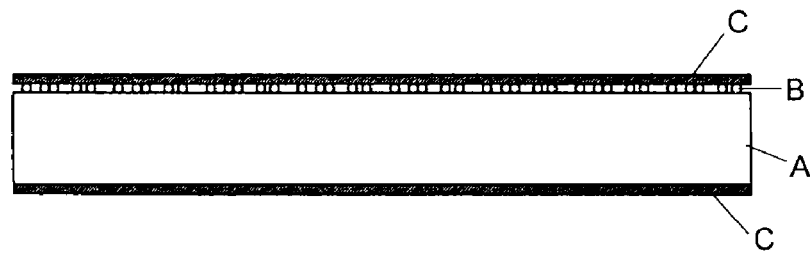
FIG. 2 is a sectional view of the volatilizing material of the present invention in which an inorganic deodorant containing zinc is carried between a fiber layer and a non-woven fabric.
Figure 3:
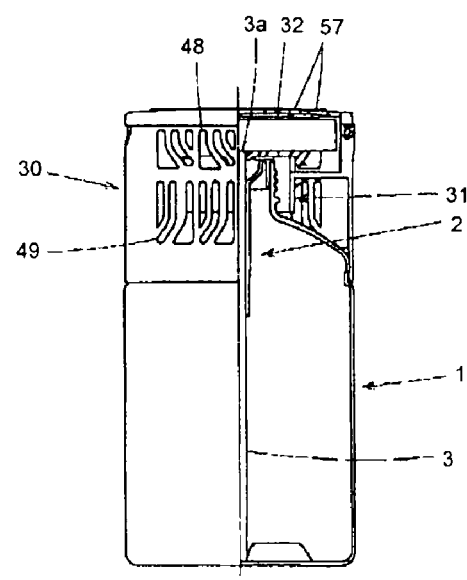
FIG. 3 is a partially cut sectional view of the deodorant/fragrant device used in Example 2.
Figure 4:
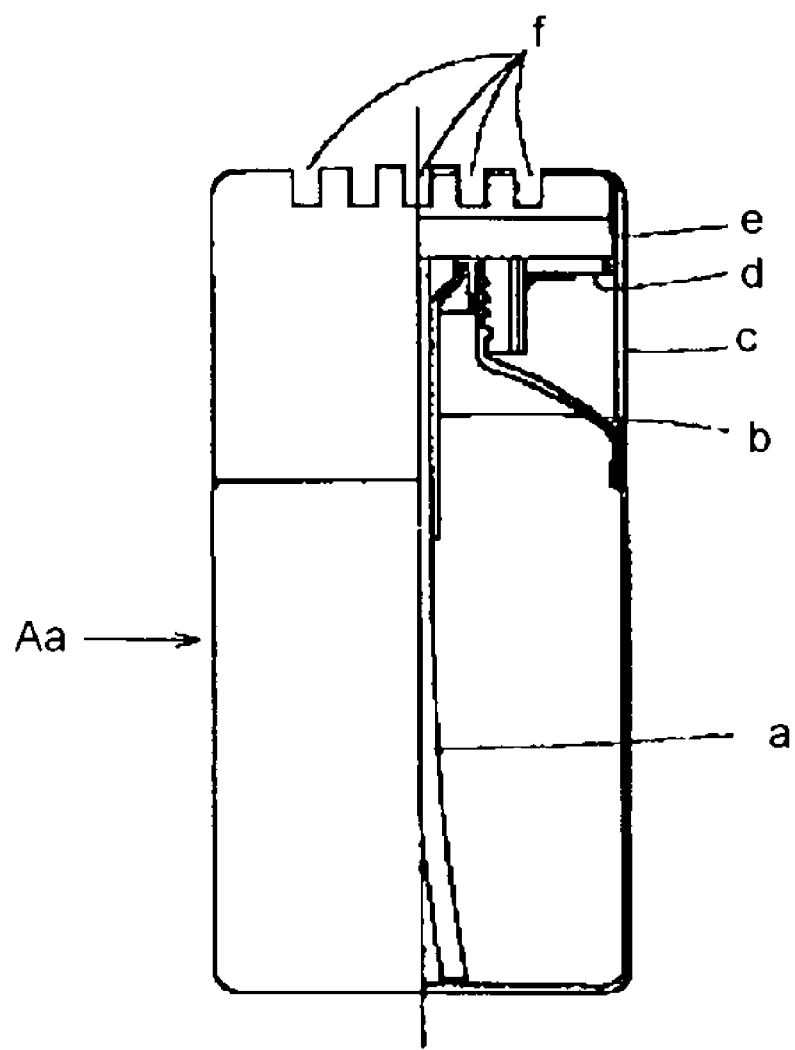
FIG. 4 is an explanatory view of the conventional deodorant/fragrant device.

| Description of Reference Numerals and Signs | |
|---|---|
| 3, a | Wick for absorbing a fragrant liquid |
| 2, b | Inner plug |
| 30, c | Covering material |
| 31, d | Supporting member |
| 32, e | Volatilizing material |
| 48, 49, 57, f | Fragrance diffusion holes |
| A | Fiber layer |
| B | Zinc compound |
| C | Non-woven fabric |

The invention claimed is:

1. A device wherein a fragrant liquid in a container is absorbed by a wick and the fragrant liquid absorbed is volatilized and released from the container through a volatilizing material placed in contact with the wick, wherein the volatilizing material comprises a zinc compound, and wherein the volatizing material is obtained by forming a laminate comprising a fiber, a heat-fusible binder and the zinc compound on a substrate, covering the resulting laminate with a covering body, and thermally compressing the laminate.

2. The device according to claim 1, wherein the zinc compound is insoluble in water.

3. The device according to claim 1, wherein the zinc compound is at least one compound selected from the group consisting of zinc oxide, zinc aluminum oxide, zinc silicate, zinc aluminum silicate and layered zinc aluminosilicate.

4. The device according to claim 1, wherein the zinc compound acts as a solid deodorant.

5. The device according to claim 1, wherein the zinc compound is present in an amount of 0.1 g/m² to 1,000 g/m².

6. The device according to claim 1, wherein the zinc compound is present in an amount of 1 g/m² to 100 g/m².

7. The device according to claim 1, wherein the zinc compound is present in an amount of 1 g/m² to 10 g/m².

8. The device according to claim 1, wherein the zinc compound has an average particle diameter of 0.1 μm to 10 mm.

9. The device according to claim 1, wherein the zinc compound has an average particle diameter of 1 μm to 1 mm.

10. The device according to claim 1, wherein the zinc compound has an average particle diameter of 1 μm to 100 μm.

11. A device, comprising a fragrant liquid in a container that is absorbed by a wick and the fragrant liquid absorbed is volatilized and released from the container through a volatilizing material placed in contact with the wick, wherein the volatilizing material comprises a zinc compound, and wherein the volatizing material is in a laminate comprising a first non-woven substrate, a fiber layer on said first non-woven substrate, the zinc compound on said fiber layer, and a second non-woven substrate on said volatizing compound on said fiber layer.

12. The device according to claim 11, wherein the zinc compound is insoluble in water.

13. The device according to claim 11, wherein the zinc compound is at least one compound selected from the group consisting of zinc oxide, zinc aluminum oxide, zinc silicate, zinc aluminum silicate and layered zinc aluminosilicate.

14. The device according to claim 11, wherein the zinc compound acts as a solid deodorant.

15. The device according to claim 11, wherein the zinc compound is present in an amount of 0.1 g/m$^2$ to 1,000 g/m$^2$.

16. The device according to claim 11, wherein the zinc compound is present in an amount of 1 g/m$^2$ to 100 g/m$^2$.

17. The device according to claim 11, wherein the zinc compound is present in an amount of 1 g/m$^2$ to 10 g/m$^2$.

18. The device according to claim 11, wherein the zinc compound has an average particle diameter of 0.1 μm to 10 mm.

19. The device according to claim 11, wherein the zinc compound has an average particle diameter of 1 μm to 1 mm.

20. The device according to claim 11, wherein the zinc compound has an average particle diameter of 1 μm to 100 μm.

* * * * *